United States Patent
Marlowe

(10) Patent No.: US 10,342,824 B2
(45) Date of Patent: Jul. 9, 2019

(54) SUPPLEMENT FOR TREATING SIDE EFFECTS OF MEDICATIONS WHICH CAUSE METABOLIC ACIDOSIS

(71) Applicant: Dr. Marlowe's Weight Loss Institute, P.L.L.C., Charlotte, NC (US)

(72) Inventor: Thomas Marlowe, Charlotte, NC (US)

( * ) Notice: Subject to any disclaimer, the term of this patent is extended or adjusted under 35 U.S.C. 154(b) by 39 days.

(21) Appl. No.: 15/652,169

(22) Filed: Jul. 17, 2017

(65) Prior Publication Data

US 2019/0015449 A1 Jan. 17, 2019

(51) Int. Cl.
| | |
|---|---|
| *A61K 9/00* | (2006.01) |
| *A23L 33/15* | (2016.01) |
| *A61K 33/10* | (2006.01) |
| *A61K 47/46* | (2006.01) |
| *A61K 31/375* | (2006.01) |

(52) U.S. Cl.
CPC .............. *A61K 33/10* (2013.01); *A23L 33/15* (2016.08); *A61K 31/375* (2013.01); *A61K 47/46* (2013.01); *A61K 9/0053* (2013.01)

(58) Field of Classification Search
CPC .... A23K 33/10; A23K 9/0053; A23K 31/375; A23K 47/46
USPC .................................................. 426/74, 648
See application file for complete search history.

(56) References Cited

U.S. PATENT DOCUMENTS

| | | | |
|---|---|---|---|
| 4,251,446 | A | 2/1981 | Crounse et al. |
| 4,289,750 | A | 9/1981 | Kopp et al. |
| 4,405,596 | A | 9/1983 | Helbig et al. |
| 4,630,727 | A | 12/1986 | Feriani et al. |
| 4,663,166 | A | 5/1987 | Veech |
| 4,851,221 | A | 7/1989 | Pak et al. |
| 5,073,389 | A * | 12/1991 | Wienecke |
| 5,149,320 | A | 9/1992 | Dhaliwal et al. |
| 5,259,985 | A | 11/1993 | Nakanishi et al. |
| 5,698,230 | A | 12/1997 | Martis et al. |
| 5,776,503 | A | 7/1998 | Martis et al. |
| 6,027,737 | A | 2/2000 | Morris, Jr. et al. |
| 6,224,917 | B1 * | 5/2001 | Murto |
| 6,399,658 | B1 | 6/2002 | Noguchi et al. |
| 6,616,939 | B1 | 9/2003 | Remesy et al. |
| 6,861,073 | B2 | 3/2005 | Tai |
| 6,887,897 | B2 | 5/2005 | Walsdorf, Sr. et al. |
| 7,862,530 | B2 | 1/2011 | Callan et al. |
| 8,383,576 | B2 | 2/2013 | Crockford et al. |
| 8,853,262 | B2 | 10/2014 | Falkenberg et al. |
| 8,864,699 | B2 | 10/2014 | Callan et al. |
| 9,393,196 | B2 | 7/2016 | Hansen |
| 9,585,941 | B2 | 3/2017 | Crockford et al. |
| 2005/0070607 | A1 | 3/2005 | Andrus et al. |
| 2008/0214456 | A1 | 9/2008 | Sosne et al. |
| 2009/0131313 | A1 | 5/2009 | Sosne et al. |
| 2009/0294360 | A1 | 12/2009 | Iwashina et al. |
| 2011/0123604 | A1 | 5/2011 | Strickland et al. |
| 2012/0071411 | A1 | 3/2012 | Crockford et al. |
| 2014/0255371 | A1 * | 9/2014 | Roberts et al. |
| 2015/0024064 | A1 * | 1/2015 | Falkenberg et al. |
| 2015/0083664 | A1 | 3/2015 | Callan et al. |
| 2015/0164128 | A1 | 6/2015 | Ibrahim et al. |
| 2015/0196708 | A1 * | 7/2015 | Mason et al. |
| 2016/0193306 | A1 * | 7/2016 | Rabovsky et al. |

FOREIGN PATENT DOCUMENTS

WO    WO 2004/048356    *   6/2004

OTHER PUBLICATIONS pURE bULK (Trademark), calcium ascorbate, What is Calcium Ascorbate Buffered Vitamin C?, pp. 105, https://purebulk.com/calcium-ascorbate-powder, pp. 1-5 (Year: 2018).*

* cited by examiner

*Primary Examiner* — Helen F Heggestad
(74) *Attorney, Agent, or Firm* — Jeffrey C. Watson; Matthew L. Grell; Grell & Watson Patent Attorneys LLC

(57) ABSTRACT

A dietary supplement for treating side effects of medication which can cause metabolic acidosis includes calcium carbonate, ascorbic acid. The calcium carbonate including a total daily calcium carbonate amount of between 100 milligrams and 10 grams of calcium carbonate. The ascorbic acid including a total daily ascorbic acid amount between 200 milligrams and 6 grams milligrams of calcium carbonate. The supplement includes a frequency of daily doses of the supplement of between 1 and 6 doses daily of the supplement. The frequency of daily doses, the total daily calcium carbonate amount, and the total daily ascorbic acid amount being set based on a titration for symptoms of a patient.

6 Claims, No Drawings

SUPPLEMENT FOR TREATING SIDE EFFECTS OF MEDICATIONS WHICH CAUSE METABOLIC ACIDOSIS

CROSS-REFERENCE TO RELATED APPLICATIONS

None

FEDERALLY SPONSORED RESEARCH OR DEVELOPMENT

None

PARTIES TO A JOINT RESEARCH AGREEMENT

None

REFERENCE TO A SEQUENCE LISTING

None

BACKGROUND OF THE DISCLOSURE

Technical Field of the Disclosure

The instant disclosure generally relates to dietary supplements. More particularly, the instant disclosure relates to a dietary supplement for treating the side effects of medications which cause metabolic acidosis. More specifically, the instant disclosure relates to a dietary supplement with the combination of Calcium Carbonate and Ascorbic Acid (Vitamin C) for treating the side effects of medications which cause metabolic acidosis.

Description of the Related Art

A dietary supplement is a product intended to add further nutritional value (supplement) to the diet. The dietary ingredient may be one, or any combination, of the following substances: vitamin, mineral, herb/botanical, amino acid, dietary substance for use by people to supplement the diet by increasing the total dietary intake, or a concentrate/metabolite/constituent/extract. U.S. authorities define dietary supplements as foods. According to the United States Food and Drug Administration (FDA), dietary supplements are products which are not pharmaceutical drugs, food additives like spices or preservatives, or conventional food, and which also meet any of these criteria:
  The product is intended to supplement a person's diet, despite it not being usable as a meal replacement;
  The product is or contains a vitamin, dietary element, herb used for herbalism or botanical used as a medicinal plant, amino acid, any substance which contributes to other food eaten, or any concentrate, metabolite, ingredient, extract, or combination of these things; or
  The product is labeled as a dietary supplement.
In the United States, the FDA has different monitoring procedures for substances depending on whether they are presented as drugs, food additives, food, or dietary supplements. Dietary supplements are eaten or taken by mouth, and are regulated in United States law as a type of food rather than a type of drug.

Metabolic acidosis is a condition that occurs when the body has excessive quantities of acid from problems in metabolism rather than problems in respiration; reasons include, but are not limited to: increased production of acid, ingestion of drugs/toxins which cause acid imbalance, kidney damage reducing clearance of acid, loss of alkaline substances (e.g. bicarbonate), and so forth. If unchecked, metabolic acidosis can lead to acidemia, i.e., blood pH is low due to increased levels of hydrogen ions in the body. Its causes are diverse, and its consequences can be serious, including eventual death. Together with respiratory acidosis, metabolic acidosis is one of the two causes of acidemia. Blood tests can be used to detect bicarbonate levels and pH levels.

Symptoms are non-specific, and clinical diagnosis can be difficult unless the patient presents with clear indications for bloodwork. Symptoms may include confusion, altered mental status, headache, coma, hyperventilation, chest pain, palpitations, heart failure, hypotension, severe anxiety due to hypercapnea, decreased visual acuity, nausea, vomiting, abdominal pain, anorexia, fatigue, muscle weakness, bone pain, and joint pain. Those in metabolic acidosis may exhibit compensatory hyperventilation (in the worst scenario, Kussmaul respirations) which is the body's mechanism of reducing excess acid levels. Rapid deep breaths increase the amount of carbon dioxide exhaled, thus lowering the serum carbon dioxide levels, and in turn the serum bicarbonate levels, resulting in some degree of compensation.

Some medications are known to cause metabolic acidosis, including, but not limited to Topiramate (Topamax®) and Zonisamide (Zonegran®). These medications and their backgrounds are discussed below.

Topiramate (brand name Topamax®) is an anticonvulsant (antiepilepsy) drug. In late 2012, topiramate was approved by the United States Food and Drug Administration (FDA) in combination with phentermine for weight loss. The drug had previously been used off-label for this purpose. Topiramate was originally produced by Ortho-McNeil Neurologics and Noramco, Inc., both divisions of the Johnson & Johnson Corporation. One adverse effect of Topiramate may be the inhibition of carbonic anhydrase, which may be strong enough to cause metabolic acidosis.

Zonisamide (brand name Zonegran®) is a sulfonamide anticonvulsant approved for use as an adjunctive therapy in adults with partial-onset seizures; infantile spasm, mixed seizure types of Lennox-Gastaut syndrome, myoclonic, and generalized tonic clonic seizure. Zonisamide has also been studied for obesity with significant positive effects on body weight loss and there are ongoing clinical trials for this indication. It is to be sold, when combined with bupropion, under the brand name Empatic®. One known adverse effect of these drugs, like zonisamide, topiramate, furosemide, and hydrochlorothiazide, may be that they can interact with other carbonic anhydrase inhibitors to increase the potential for metabolic acidosis.

Currently there are no known dietary supplements that are effective at mitigating and/or preventing and/or reducing the side-effects of medications which can cause metabolic acidosis, including, but not limited to, Topiramate (Topamax®), Zonisamide (Zonegran®), furosemide, hydrochlorothiazide, the like, or combinations thereof.

The instant disclosure of a supplement for treating side effects of medications which may cause metabolic acidosis is designed to address at least some aspects of the problems discussed above.

SUMMARY

Briefly described, in a possibly preferred embodiment, the present disclosure overcomes the above-mentioned disadvantages and meets the recognized need for such a device by providing a supplement, or dietary supplement, that may be for treating the side-effects of medications which may cause metabolic acidosis. In general, the supplement may include calcium carbonate and ascorbic acid (also known as Vitamin C). This combination of ingredients may provide a supplement for mitigating, preventing, or reducing side-effects of medications which can cause metabolic acidosis.

In select embodiments, the calcium carbonate may include a total daily calcium carbonate amount between 100 milligrams and 10 grams of calcium carbonate. As an example, and clearly not limited thereto, the total daily calcium carbonate amount may be approximately 375 milligrams of calcium carbonate.

In select embodiments, the ascorbic acid may include a total daily ascorbic acid amount between 200 milligrams and 6 grams of ascorbic acid. As an example, and clearly not limited thereto, the total daily ascorbic acid amount may be approximately 250 milligrams of ascorbic acid.

In select embodiments, the supplement of the instant disclosure may include a total daily calcium carbonate amount between 100 milligrams and 10 grams of calcium carbonate, and a total daily ascorbic acid amount between 200 milligrams and 6 grams of ascorbic acid. As an example, and clearly not limited thereto, the supplement of the instant disclosure may include the total daily calcium carbonate amount of approximately 375 milligrams of calcium carbonate, and the total daily ascorbic acid amount may be approximately 250 milligrams of ascorbic acid.

One feature of the supplement of the instant disclosure may be that it can include a frequency of daily doses. As examples, and clearly not limited thereto, the frequency of daily doses may be between 1 and 6 doses daily of the supplement.

In select embodiments, the frequency of daily doses, the total daily calcium carbonate amount, and the total daily ascorbic acid amount may be set based on a titration for symptoms of a patient, titration based upon lab values or lab abnormalities, or combinations thereof. The titration for symptoms of the patient for setting the frequency of daily doses, the total daily calcium carbonate amount, and the total daily ascorbic acid amount may be for seeking to protect the creation of a combination of calcium carbonate and ascorbic acid in the patient for mitigating, preventing, or reducing the side effects of medications which can cause metabolic acidosis of the patient. These side-effects of the medications may be, but are not limited to: cognitive impairment; difficulty finding the right word; expressive aphasia; fatigue; slurred speech; drowsiness; paresthesias; difficulty concentrating; memory difficulties; mood disturbances; sleep disturbance; the like; and combinations thereof.

In select embodiments, the supplement may be for reducing the side-effects of topiramate, zonisamide, furosemide, hydrochlorothiazide, the like, or combinations thereof.

In one aspect, the supplement of the instant disclosure may include the calcium carbonate including a total daily calcium carbonate amount of 375 milligrams of calcium carbonate, the ascorbic acid including a total daily ascorbic acid amount of 250 milligrams of ascorbic acid, and the frequency being between 1 and 6 doses daily of the supplement. This specific combination of ingredients and frequencies of the supplement may be for mitigating, preventing, or reducing side-effects of medications which can cause metabolic acidosis. In this embodiment, the frequency of daily doses, the total daily calcium carbonate amount, and the total daily ascorbic acid amount may be set based on a titration for symptoms of a patient. In this embodiment, the titration for symptoms of a patient for setting the frequency of daily doses, the total daily calcium carbonate amount, and the total daily ascorbic acid amount may be for seeking to protect the creation of a combination of calcium carbonate and ascorbic acid in the patient for mitigating, preventing, or reducing the side effects of medications which can cause metabolic acidosis. These side-effects of the medications may be, but are not limited to: cognitive impairment; difficulty finding the right word; expressive aphasia; fatigue; slurred speech; drowsiness; paresthesias; difficulty concentrating; memory difficulties; mood disturbances; sleep disturbance; the like; and combinations thereof. As examples, and clearly not limited thereto, the supplement may be for reducing the side-effects of topiramate, zonisamide, furosemide, hydrochlorothiazide, the like, and/or combinations thereof. In other embodiments, the frequency of daily doses, the total daily calcium carbonate amount, and the total daily ascorbic acid amount may be set based on a titration based upon lab values or lab abnormalities.

In another aspect of the instant disclosure, a method of treating side effects of medications which may cause metabolic acidosis may be included. This method may generally include the steps of ingesting the supplement in any of the various embodiments shown and/or described herein. In select embodiments, the supplement ingested in the instant method may include calcium carbonate, and ascorbic acid. As such, the supplement ingested may be for mitigating, preventing, or reducing side-effects of medications which can cause metabolic acidosis.

In select embodiments of the method disclosed herein for treating side effects of medications which may cause metabolic acidosis, the calcium carbonate may include a total daily calcium carbonate amount between 100 milligrams and 10 grams of calcium carbonate, and the ascorbic acid may include a total daily ascorbic acid amount between 200 milligrams and 6 grams of ascorbic acid. As an example, and clearly not limited thereto, the calcium carbonate may include a total daily calcium carbonate amount of approximately 375 milligrams of calcium carbonate, and the ascorbic acid may include a total daily ascorbic acid amount of approximately 250 milligrams of ascorbic acid.

In select embodiments of the method disclosed herein for treating side effects of medications which may cause metabolic acidosis, the step of ingesting the supplement may include ingesting the supplement at a frequency of daily doses of the supplement. As examples, and clearly not limited thereto, the frequency of daily does may be between 1 and 6 doses daily of the supplement.

In other select embodiments of the method disclosed herein for treating side effects of medications which may cause metabolic acidosis, the method may further comprise the step of setting the frequency of daily doses, the total daily calcium carbonate amount, and the total daily ascorbic acid amount based on a titration for symptoms of a patient. In this embodiment, the titration for symptoms of the patient for setting the frequency of daily doses, the total daily calcium carbonate amount, and the total daily ascorbic acid amount, may be for seeking to protect the creation of a combination of calcium carbonate and ascorbic acid in the patient for mitigating, preventing, or reducing the side effects of medications which can cause metabolic acidosis of the patient. In other embodiments, the frequency of daily doses, the total daily calcium carbonate amount, and the total daily ascorbic acid amount may be set based on a titration based upon lab values or lab abnormalities.

In other select embodiments of the method disclosed herein for treating side effects of medications which may cause metabolic acidosis, the side-effects of the medications may be selected from, but are not limited to: cognitive impairment; difficulty finding the right word; expressive aphasia; fatigue; slurred speech; drowsiness; paresthesias; difficulty concentrating; memory difficulties; mood disturbances; sleep disturbance; the like; and combinations thereof.

In other select embodiments of the method disclosed herein for treating side effects of medications which may cause metabolic acidosis the supplement may be for reducing the side-effects of topiramate, zonisamide, furosemide, hydrochlorothiazide, the like, and/or combinations thereof.

These and other features of the supplement for treating side effects of medications which may cause metabolic acidosis will become more apparent to one skilled in the art from the prior Summary, and the following Detailed Description, and Claims.

DETAILED DESCRIPTION

In describing the exemplary embodiments of the present disclosure, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples, and are merely examples among other possible examples.

By way of example, and not limitation, herein is described example embodiments of a supplement, or dietary supplement, that may be for treating the side-effects of medications which may cause metabolic acidosis. In general, the supplement may include calcium carbonate and ascorbic acid (also known as Vitamin C). This combination of ingredients may provide a supplement for mitigating, preventing, or reducing side-effects of medications which can cause metabolic acidosis.

Calcium carbonate may be included in the supplement disclosed herein that may be for treating the side-effects of medications which may cause metabolic acidosis. Calcium carbonate may be a chemical compound with the formula $CaCO_3$. Calcium carbonate may be a common substance found in rocks as the minerals calcite and aragonite (most notably as limestone, which contains both of those minerals) and is the main component of pearls and the shells of marine organisms, snails, and eggs. In select embodiments, calcium carbonate may be in the form of coral calcium. Coral calcium is a salt of calcium derived from fossilized coral reefs (primarily from limestone and coastal deposits). Calcium carbonate may be the active ingredient in agricultural lime and may be created when calcium ions in hard water react with carbonate ions to create limescale. Calcium carbonate may be widely used medicinally as an inexpensive dietary calcium supplement for gastric antacid (e.g., Tums®). Calcium carbonate may also be used as a phosphate binder for the treatment of hyperphosphatemia (primarily in patients with chronic renal failure). Calcium carbonate may also be known in the pharmaceutical industry as an inert filler for tablets and other pharmaceuticals. Calcium carbonate may be used in the production of calcium oxide as well as toothpaste and has seen a resurgence as a food preservative and color retainer, when used in or with products such as organic apples. However, excess calcium from supplements, fortified food and high-calcium diets, can cause milk-alkali syndrome, which has serious toxicity and can be fatal. As a food additive, calcium carbonate may be designated E170; INS number 170. In select embodiments, the calcium carbonate may include a total daily calcium carbonate amount between 100 milligrams and 10 grams of calcium carbonate. As an example, and clearly not limited thereto, the total daily calcium carbonate amount may be approximately 375 milligrams of calcium carbonate.

Ascorbic acid, also known as Vitamin C and L-ascorbic acid, may be included in the supplement disclosed herein that may be a vitamin found in food and used as a dietary supplement. For example, as a supplement, ascorbic acid may be known to be used to treat and prevent scurvy. Ascorbic acid may be ingested by mouth or by injection. Ascorbic acid may be generally well tolerated. However, large doses may cause gastrointestinal discomfort, headache, trouble sleeping, and flushing of the skin. Ascorbic acid is known as an essential nutrient involved in the repair of tissue. Foods that contain ascorbic acid include, but are not limited to, citrus fruit, tomatoes, red peppers, and potatoes. Ascorbic acid is available as a generic supplement and over the counter. In select embodiments, the ascorbic acid may include a total daily ascorbic acid amount between 200 milligrams and 6 grams of ascorbic acid. As an example, and clearly not limited thereto, the total daily ascorbic acid amount may be approximately 250 milligrams of ascorbic acid.

In select embodiments, the supplement of the instant disclosure may include a total daily calcium carbonate amount between 100 milligrams and 10 grams of calcium carbonate, and a total daily ascorbic acid amount between 200 milligrams and 6 grams of ascorbic acid. As an example, and clearly not limited thereto, the supplement of the instant disclosure may include the total daily calcium carbonate amount of approximately 375 milligrams of calcium carbonate, and the total daily ascorbic acid amount may be approximately 250 milligrams of ascorbic acid. The supplement disclosed herein may be provided in a variety of forms, including, but not limited to, traditional tablets, capsules, liquids, and powders, as well as drinks and energy bars.

One feature of the supplement of the instant disclosure may be that it can include a frequency of daily doses. As examples, and clearly not limited thereto, the frequency of daily doses may be between 1 and 6 doses daily of the supplement. As an example, if a doctor were to recommend the total daily calcium carbonate amount of approximately 375 milligrams of calcium carbonate, and the total daily ascorbic acid amount of approximately 250 milligrams of ascorbic acid, the supplement may be provided in, but is not limited to:

A single-frequency dosage (tablets, capsules, liquids, and powders, as well as drinks and energy bars) with the combination of 375 milligrams of calcium carbonate, and 250 milligrams of ascorbic acid;

A two-frequency dosage (tablets, capsules, liquids, and powders, as well as drinks and energy bars) with each dose having the combination of 375 milligrams of calcium carbonate, and 250 milligrams of ascorbic acid, for a total daily dose of 750 milligrams calcium carbonate and a total daily dose of 500 milligrams of ascorbic acid;

A three-frequency dosage (tablets, capsules, liquids, and powders, as well as drinks and energy bars) with each dose having the combination of 375 milligrams of calcium carbonate, and 250 milligrams of ascorbic acid, for a total daily dose of 1.125 grams calcium carbonate and a total daily dose of 750 milligrams of ascorbic acid;

A four-frequency dosage (tablets, capsules, liquids, and powders, as well as drinks and energy bars) with each dose having the combination of 375 milligrams of calcium carbonate, and 250 milligrams of ascorbic acid, for a total daily dose of 1.5 grams calcium carbonate and a total daily dose of 1.0 grams of ascorbic acid;

A five-frequency dosage (tablets, capsules, liquids, and powders, as well as drinks and energy bars) with each dose having the combination of 375 milligrams of calcium carbonate, and 250 milligrams of ascorbic acid, for a total daily dose of 1.875 grams calcium carbonate and a total daily dose of 1.25 grams of ascorbic acid; and/or A six-frequency dosage (tablets, capsules, liquids, and powders, as well as drinks and energy bars) with each dose having the combination of 375 milligrams of calcium carbonate, and 250 milligrams of ascorbic acid, for a total daily dose of 2.25 grams calcium carbonate and a total daily dose of 1.5 grams of ascorbic acid.

In select embodiments of the supplement disclosed herein, the frequency of daily doses, the total daily calcium carbonate amount, and the total daily ascorbic acid amount may be set based on a titration for symptoms of a patient. The titration for symptoms of the patient for setting the frequency of daily doses, the total daily calcium carbonate amount, and the total daily ascorbic acid amount may be for seeking to protect the creation of a combination of calcium carbonate and ascorbic acid in the patient for mitigating, preventing, or reducing the side effects of medications which can cause metabolic acidosis of the patient. These side-effects of the medications may be, but are not limited to: cognitive impairment; difficulty finding the right word; expressive aphasia; fatigue; slurred speech; drowsiness; paresthesias; difficulty concentrating; memory difficulties; mood disturbances; sleep disturbance; the like; and combinations thereof. In select embodiments, the supplement may be for reducing the side-effects of topiramate, zonisamide, furosemide, hydrochlorothiazide, the like, other similar medications or diets, and/or combinations thereof.

In other embodiments, the frequency of daily doses, the total daily calcium carbonate amount, and the total daily ascorbic acid amount may be set based on a titration based upon lab values or lab abnormalities. As an example, treating doctors/NP's/PA's might decide to titrate based upon a patient's bicarb levels instead of clinically titrating based upon symptoms.

In sum, the instant supplement may be the combination of Calcium Carbonate and Ascorbic Acid (Vitamin C) with the purpose of mitigating and/or preventing and/or reducing the side-effects of medications which can cause metabolic acidosis (including, but not limited to, Topamax® and Zonegran®). Some of those side-effects due to metabolic acidosis include, but are not limited to: cognitive impairment, difficulty finding the right word, expressive aphasia, fatigue, slurred speech, drowsiness, paresthesias, difficulty concentrating, memory difficulties, mood disturbances, and sleep disturbance. One possible dose combination is 375 mg of Calcium Carbonate and 250 mg of Ascorbic Acid (Vitamin C) per serving, with patients taking 1-6 doses daily, but the total daily dose which is effective can be different for each patient. The total daily dose of calcium carbonate can range from 100 mg to 10 gms and will depend on titration for symptoms. The total daily dose of Ascorbic Acid can range from 200 mg to 6 gms and will depend on titration for symptoms. As such, the instant supplement is designed as a combination of Calcium Carbonate and Ascorbic Acid (Vitamin C) specifically for the purpose of mitigating and/or preventing and/or reducing the side-effects of medications which can cause metabolic acidosis.

In addition to the supplement, a method of treating side effects of medications which may cause metabolic acidosis is contemplated with the instant disclosure. This method disclosed herein of treating side effects of medications which may cause metabolic acidosis may generally include the steps of ingesting the supplement, or dietary supplement, that may be for treating the side-effects of medications which may cause metabolic acidosis, in any of the various embodiments shown and/or described herein. As such, the supplement ingested in the instant method may include calcium carbonate, and ascorbic acid. As such, the supplement ingested may be for mitigating, preventing, or reducing side-effects of medications which can cause metabolic acidosis.

In select embodiments of the method disclosed herein for treating side effects of medications which may cause metabolic acidosis, the calcium carbonate may include a total daily calcium carbonate amount between 100 milligrams and 10 grams of calcium carbonate, and the ascorbic acid may include a total daily ascorbic acid amount between 200 milligrams and 6 grams of ascorbic acid. As an example, and clearly not limited thereto, the calcium carbonate may include a total daily calcium carbonate amount of approximately 375 milligrams of calcium carbonate, and the ascorbic acid may include a total daily ascorbic acid amount of approximately 250 milligrams of ascorbic acid.

In select embodiments of the method disclosed herein for treating side effects of medications which may cause metabolic acidosis, the step of ingesting the supplement may include ingesting the supplement at a frequency of daily doses of the supplement. As examples, and clearly not limited thereto, the frequency of daily does may be between 1 and 6 doses daily of the supplement. As such, the step of ingesting the supplement may include, but is clearly not limited thereto, ingesting the supplement as follows:

Ingesting the supplement in a single-frequency dosage (tablets, capsules, liquids, and powders, as well as drinks and energy bars) with the combination of 375 milligrams of calcium carbonate, and 250 milligrams of ascorbic acid;

Ingesting the supplement in a two-frequency dosage (tablets, capsules, liquids, and powders, as well as drinks and energy bars) with each dose having the combination of 187.5 milligrams of calcium carbonate, and 125 milligrams of ascorbic acid;

Ingesting the supplement in a three-frequency dosage (tablets, capsules, liquids, and powders, as well as drinks and energy bars) with each dose having the combination of 125 milligrams of calcium carbonate, and 83.33 milligrams of ascorbic acid;

Ingesting the supplement in a four-frequency dosage (tablets, capsules, liquids, and powders, as well as drinks and energy bars) with each dose having the combination of 93.75 milligrams of calcium carbonate, and 62.5 milligrams of ascorbic acid;

Ingesting the supplement in a five-frequency dosage (tablets, capsules, liquids, and powders, as well as drinks and energy bars) with the combination of 75 milligrams of calcium carbonate, and 50 milligrams of ascorbic acid; and/or Ingesting the supplement in a six-frequency dosage (tablets, capsules, liquids, and powders, as well as drinks and energy bars) with the combination of 375 milligrams of calcium carbonate, and 250 milligrams of ascorbic acid.

In other select embodiments of the method disclosed herein for treating side effects of medications which may cause metabolic acidosis, the method may further comprise the step of setting the frequency of daily doses, the total daily calcium carbonate amount, and the total daily ascorbic acid amount based on a titration for symptoms of a patient. In this embodiment, the titration for symptoms of the patient for setting the frequency of daily doses, the total daily calcium carbonate amount, and the total daily ascorbic acid amount, may be for seeking to protect the creation of a combination of calcium carbonate and ascorbic acid in the patient for mitigating, preventing, or reducing the side effects of medications which can cause metabolic acidosis of the patient.

In other select embodiments of the method disclosed herein for treating side effects of medications which may cause metabolic acidosis, the side-effects of the medications may be selected from, but are not limited to: cognitive impairment; difficulty finding the right word; expressive aphasia; fatigue; slurred speech; drowsiness; paresthesias; difficulty concentrating; memory difficulties; mood disturbances; sleep disturbance; the like; and combinations thereof.

In other select embodiments of the method disclosed herein for treating side effects of medications which may cause metabolic acidosis the supplement may be for reducing the side-effects of topiramate, zonisamide, furosemide, hydrochlorothiazide, the like, and/or combinations thereof.

The foregoing description comprises illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions. Although specific terms may be employed herein, they are used in a generic and descriptive sense only and not for purposes of limitation. Accordingly, the present disclosure is not limited to the specific embodiments described herein, but is limited only by the following claims.

What is claimed is:

1. A method of treating side effects of medications which cause metabolic acidosis including:
   recognizing a patient that has been taking the medications which cause metabolic acidosis for side effects caused by the medications which causes metabolic acidosis, wherein the side-effects of said medications being selected from a group consisting of: cognitive impairment including difficulty finding the right word, expressive aphasia fatigue, or slurred speech; drowsiness; paresthesias; difficulty concentrating; memory difficulties; mood disturbances; sleep disturbance; and combinations thereof;
   determining:
      a titration for symptoms of the patient,
      a titration based upon lab values or lab abnormalities; or
      combinations thereof;
   providing a supplement comprising calcium carbonate, and ascorbic acid;
   wherein, said supplement being for mitigating, preventing, or reducing the side-effects of the medications which cause metabolic acidosis;
   setting a frequency of daily doses between 1 and 6 doses daily based on the titration for symptoms of the patient, the titration based upon lab values or lab abnormalities, or combinations thereof;
   setting a total daily calcium carbonate amount from the supplement of between 100 milligrams and 10 grams of calcium carbonate based on the titration for symptoms of the patient, the titration based upon lab values or lab abnormalities, or combinations thereof;
   setting a total daily ascorbic acid amount from the supplement of between 200 milligrams and 6 grams of ascorbic acid based on the titration for symptoms of the patient, the titration based upon lab values or lab abnormalities, or combinations thereof;
   wherein the titration for symptoms of the patient for setting said frequency of daily doses, said total daily calcium carbonate amount, and said total daily ascorbic acid amount being for seeking to protect the creation of a combination of calcium carbonate and ascorbic acid in the patient for mitigating, preventing, or reducing the side effects of the medications which cause metabolic acidosis of the patient;
   ingesting the supplement including:
      ingesting the set total daily calcium carbonate amounts;
      ingesting the set total daily ascorbic acid amount; and
      ingesting the supplement at the set frequency of daily doses.

2. The method of claim 1, wherein:
   said calcium carbonate including a total daily calcium carbonate amount of approximately 375 milligrams of calcium carbonate; and
   said ascorbic acid including a total daily ascorbic acid amount of approximately 250 milligrams of ascorbic acid.

3. A method of treating side effects of medications which cause metabolic acidosis including:
   providing a supplement comprising calcium carbonate, and ascorbic acid, wherein, said supplement being for mitigating, preventing, or reducing the side-effects of medications which cause metabolic acidosis in a patient;
   determining:
      a titration for symptoms of the patient,
      a titration based upon lab values or lab abnormalities; or
      combinations thereof;
   setting a frequency of daily doses, a total daily calcium carbonate amount, and a total daily ascorbic acid amount based on the titration for symptoms of the patient for seeking to protect the creation of a combination of calcium carbonate and ascorbic acid in the patient; and
   mitigating, preventing, or reducing the side effects of the medications which cause metabolic acidosis of the patient via the provided supplement.

4. The method of claim 3 further including:
   recognizing the patient has been taking the medications which cause metabolic acidosis for side effects caused by the medications which causes metabolic acidosis, wherein the side-effects of said medications being selected from a group consisting of: cognitive impairment including difficulty finding the right word, expressive aphasia fatigue, or slurred speech; drowsiness; paresthesias; difficulty concentrating; memory difficulties; mood disturbances; sleep disturbance; and combinations thereof.

5. The method of claim 3 further including:
setting a frequency of daily doses between 1 and 6 doses daily based on the titration for symptoms of the patient, the titration based upon lab values or lab abnormalities, or combinations thereof;
setting a total daily calcium carbonate amount from the supplement of between 100 milligrams and 10 grams of calcium carbonate based on the titration for symptoms of the patient, the titration based upon lab values or lab abnormalities, or combinations thereof; and
setting a total daily ascorbic acid amount from the supplement of between 200 milligrams and 6 grams of ascorbic acid based on the titration for symptoms of the patient, the titration based upon lab values or lab abnormalities, or combinations thereof.

6. The method of claim 5, wherein:
said calcium carbonate including a total daily calcium carbonate amount of approximately 375 milligrams of calcium carbonate; and
said ascorbic acid including a total daily ascorbic acid amount of approximately 250 milligrams of ascorbic acid.

* * * * *